United States Patent
Howard et al.

(10) Patent No.: US 9,708,571 B2
(45) Date of Patent: Jul. 18, 2017

(54) REDUCED COLOR EPOXIDIZED ESTERS FROM EPOXIDIZED NATURAL FATS AND OILS

(75) Inventors: Stephen Howard, Sherman, IL (US); Erik Hagberg, Decatur, IL (US); George Poppe, Forsyth, IL (US)

(73) Assignee: Archer Daniels Midland Company, Decatur, IL (US)

( * ) Notice: Subject to any disclaimer, the term of this patent is extended or adjusted under 35 U.S.C. 154(b) by 824 days.

(21) Appl. No.: 14/125,602

(22) PCT Filed: May 21, 2012

(86) PCT No.: PCT/US2012/038760
§ 371 (c)(1),
(2), (4) Date: Dec. 12, 2013

(87) PCT Pub. No.: WO2013/002913
PCT Pub. Date: Jan. 3, 2013

(65) Prior Publication Data
US 2014/0113999 A1   Apr. 24, 2014

Related U.S. Application Data

(60) Provisional application No. 61/501,312, filed on Jun. 27, 2011.

(51) Int. Cl.
| | |
|---|---|
| *C11C 3/10* | (2006.01) |
| *C11C 1/08* | (2006.01) |
| *C07D 303/42* | (2006.01) |
| *C08K 5/10* | (2006.01) |
| *C11B 3/02* | (2006.01) |

(52) U.S. Cl.
CPC ............. *C11C 3/10* (2013.01); *C07D 303/42* (2013.01); *C08K 5/10* (2013.01); *C11B 3/02* (2013.01); *C11C 1/08* (2013.01)

(58) Field of Classification Search
CPC ............................... C07D 303/42; C07C 67/03
USPC ......................................................... 524/318
See application file for complete search history.

(56) References Cited

U.S. PATENT DOCUMENTS

| | | | | |
|---|---|---|---|---|
| 3,070,608 A | * | 12/1962 | Kuester ................ | C07D 303/42 549/539 |
| 2005/0159610 A1 | * | 7/2005 | Poppe .................... | C07C 67/03 554/174 |

OTHER PUBLICATIONS

Brown, Organic Synthesis via Boranes, John Wiley & Son, Inc. p. 260 (1975).*

* cited by examiner

*Primary Examiner* — Ling Choi
*Assistant Examiner* — Thuy-Ai N Nguyen
(74) *Attorney, Agent, or Firm* — William B. Miller

(57) ABSTRACT

Reduced color epoxidized fatty acid esters are provided which may be used as primary plasticizers for PVC, in replacement of phthalate plasticizers. The reduced color epoxidized fatty acid esters are prepared from natural fats or oils by transesterification and interesterification processes, whereby through the use of borohydride, materials having Pt—Co colors according to ASTM D1209 on the order of 50 and lower are possible.

22 Claims, No Drawings

REDUCED COLOR EPOXIDIZED ESTERS FROM EPOXIDIZED NATURAL FATS AND OILS

The present invention is directed to processes for making epoxidized fatty acid esters from various animal fats and plant oils, and to the products made by those processes. In particular, the present invention concerns methods for making epoxidized fatty acid esters with low color from epoxidized natural animal fats and plant oils ("natural fats and oils").

Such epoxidized fatty acid esters have lately been of considerable interest for use as renewable source-based or—derived plasticizers for various polymer compositions and end uses. In particular, such materials have been investigated for use in polyvinyl halide compositions.

Polyvinyl chloride (PVC), the most common vinyl halide polymer, finds commercial application in a rigid, substantially unplasticized form and in a plasticized PVC form. Rigid PVC, with which the present invention is not concerned, is used for pipework, ducts and the like in which high chemical resistance is needed but not flexibility or pliability. Plasticized PVC, on the other hand, finds application in films, sheeting, wire and cable coverings, moldings, conveyor belting, toys and hose, in addition to serving as a leather substitute and as a fabric covering for upholstered furniture, automotive seating and other articles.

Broadly speaking, plasticizers are materials which are combined with polymers such as polyvinyl chloride (hereinafter, PVC) to impart flexibility, extensibility and workability or some combination of these attributes to the polymer, as needed for a particular end use. Frequently, a combination of primary and secondary plasticizers is used, with the secondary plasticizers not acting in and of themselves to impart the desired attributes to the PVC but serving to improve the effectiveness of the primary plasticizer(s) and optionally offering other characteristics to a PVC composition in which the materials are incorporated.

Historically, the majority of primary PVC plasticizers have been petroleum-derived phthalates and benzoate compounds, dioctyl phthalate and diisononyl phthalate being notable examples. However, such petroleum-derived plasticizers are frequently expensive to produce and use because of fluctuations in the pricing and availability of petroleum, and are increasingly likely to remain so as petroleum reserves are reduced and new supplies prove more costly and difficult to secure. Further, certain of the petroleum-derived phthalate plasticizers have raised concerns for their potential to disrupt human endocrine activity, and regulatory controls have been established in a number of countries to address these concerns.

Unmodified plant/vegetable oils are largely incompatible with PVC resin, but certain modified derivatives of such oils, such as epoxidized soybean oil (ESO), are compatible with PVC resin and have been actively investigated for use as a lower cost, renewable source-based alternative to the petroleum-based plasticizers, both as primary and secondary plasticizers. The interest in developing useful plasticizers from renewable sources, such as animal fats or especially plant/vegetable oils, has developed partly also from the expectation that such materials would be less likely to cause physiological disturbances or other injuries to persons coming into contact with products which require plasticizers in their composition.

As related in U.S. Pat. No. 6,797,753 to Benecke et al., however, these modified vegetable oil derivatives have been used to a limited extent commercially as secondary plasticizers only, because of compatibility limitations in PVC. Benecke et al. and others have accordingly sought to identify further modifications or other vegetable oil-derived materials with improved compatibility for use as a primary plasticizer, while retaining the beneficial thermal stabilization properties of epoxidized soybean oil. In Benecke et al., primary plasticizers are reported where the plasticizers contain fatty acids derived from vegetable oils and the fatty acids are substantially fully esterified with an alcohol (monool or polyol), the fatty acids have unsaturated bonds that are substantially fully epoxidized, and the fatty acids are added substantially randomly to one or more hydroxyl sites on the alcohol. Primary plasticizers particularly mentioned include epoxidized pentaerythritol tetrasoyate, epoxidized propylene glycol disoyate, epoxidized ethylene glycol disoyate, epoxidized methyl soyate, epoxidized sucrose octasoyate and the epoxidized product of soybean oil interesterified with linseed oil.

Benecke et al. describe several methods by which these plasticizers may be made. In one embodiment, found at column 3, lines 17-30 of the '753 patent, the vegetable oil fatty acids are linked by direct esterification to monoalcohols or polyalcohols, and the esterified products are then epoxidized. In a second embodiment described starting at line 30, the direct esterification step is replaced with transesterification, whereby the monool or polyol reacts with a lower alkyl ester of a vegetable oil fatty acid to produce the desired ester plus a lower alcohol, and the ester is then epoxidized. In yet another embodiment, a first ester is interesterified with a second ester, and the desired ester is again epoxidized.

WO 2009/102877A1, published Aug. 20, 2009 for "A Replacement Plasticizer System for Phthalate-Plasticized Formulations", is similarly directed, describing epoxidized fatty acid esters useful as primary plasticizers in a phthalate-free system and which are suitably nonvolatile, not petroleum-based, and capable of imparting thermal stability to formulations presently using phthalate plasticizers, including those based on PVC, other halogenated polymers, acid-functionalized polymers, anhydride-functionalized polymers, and nitrile rubbers. Suitable epoxidized fatty acid ester plasticizers are said to include epoxidized biodiesel (conventionally, fatty acid methyl esters of soy, rapeseed or palm oils, though $C_1$-$C_{14}$ esters are more generally contemplated) and epoxidized derivatives of fatty acid esters of biodiesel. Methods described for making the epoxidized fatty acid esters, as in Benecke et al., involve formation of the fatty acid ester first, followed by epoxidation of the ester.

Epoxidized methyl soyate esters—as prominently featured in both Benecke et al. and the WO'877 application just discussed—have also been known to be made starting from epoxidized soybean oil by alcoholysis, see U.S. Pat. No. 3,070,608 to Kuester et al., for example, wherein ESO (epoxidized soybean oil) is reacted with a molar excess of methanol in the presence of sodium methoxide as a catalyst, to produce EMS. The total epoxide content in going from ESO to EMS is indicated at column 1, lines 21-22, as being relatively unchanged, showing "little or no decrease".

As has been mentioned, the various renewable source-based plasticizers which have been described in these and in other references have been developed, at least in part, with an objective of providing drop-in replacements for the current phthalate plasticizers. In respect of a number of attributes, the epoxidized fatty acid ester plasticizers made by these known methods can in fact demonstrate substantially equivalent, or certainly, commercially acceptable, levels of performance when compared to the phthalate plasticizers they seek to replace.

One very important attribute is color. In certain common applications or contexts of use, the plasticized compositions are desirably both colorless and clear. An example would be in the making of clear plastic tubing for medical and other uses. In a great many other applications, where a pigmented composition is used (and the desired end color is other than black), a low color plasticizer is likewise needed to enable the desired colors to be achieved. Examples would include toys, automotive interior and exterior trim, textile inks, vinyl flooring (which requires a non-yellow wear layer and clean whites underneath) and myriad other consumer and industrial goods where color is an important differentiator and marketing tool. The phthalate plasticizers which have heretofore been so widely used have Pt—Co colors in the range of 10-20, and while none of Benecke et al, Kuester et al. or the WO'877 application explicitly indicates the Pt—Co color of the epoxidized esters made in each, we have found in making epoxidized methyl soyate plasticizers by methods as described in the WO'877 application and in Benecke et al. that the Pt—Co color values are higher than those associated with the phthalate plasticizers—so that improvement in this important attribute was needed.

The present invention in one aspect addresses this need, in providing a process for making a reduced color epoxidized fatty acid ester from an epoxidized natural fat or oil, by combining an alcohol, an epoxidized natural fat or oil and borohydride with a transesterification catalyst under conditions which are effective for reacting the alcohol and epoxidized natural fat or oil to form an epoxidized fatty acid ester exhibiting a reduced Pt—Co color, as compared to the epoxidized fatty acid ester that would result from reacting the epoxidized natural fat or oil and the alcohol in the presence of the catalyst and under the same conditions but without the use of borohydride. In one embodiment, borohydride is included in the reaction mixture with the epoxidized natural fat or oil and alcohol before introducing the catalyst. In an alternative embodiment, borohydride and catalyst are concurrently or substantially concurrently incorporated in the reaction mixture with the epoxidized natural fat or oil and alcohol. In still another embodiment, borohydride can be incorporated in the reaction mixture both prior to and concurrently with the introduction of the catalyst. In any case, the borohydride is generally a lesser component of the reaction mixture as compared to the catalyst. In a related aspect, the present invention is directed to the reduced color epoxidized fatty acid esters made by such a process, and to the plasticized polymer compositions including a reduced color epoxidized fatty acid ester as a primary plasticizer, especially to plasticized polymer compositions which are phthalate- or substantially phthalate-free and include the reduced color epoxidized fatty acid esters of the present invention as phthalate replacement primary plasticizers.

In a second aspect, the present invention concerns a process for making a reduced color epoxidized fatty acid ester or blend of such esters, by combining an epoxidized natural fat or oil, a second ester and borohydride with an interesterification catalyst under conditions which are effective for reacting the second ester and epoxidized natural fat or oil to form one or more epoxidized fatty acid esters exhibiting a reduced Pt—Co color, as compared to the epoxidized fatty acid ester or esters that would result from reacting the epoxidized natural fat or oil and the second ester in the presence of the catalyst and under the same conditions but without the use of borohydride. In one embodiment, borohydride is included in the reaction mixture with the epoxidized natural fat or oil and the second ester before introducing the catalyst. In an alternative embodiment, borohydride and catalyst are concurrently or substantially concurrently incorporated in the reaction mixture with the epoxidized natural fat or oil and second ester. In still another embodiment, borohydride can be incorporated in the reaction mixture both prior to and concurrently with the introduction of the catalyst. In any case, the borohydride is generally a lesser component of the reaction mixture as compared to the catalyst. In related aspects, reduced color epoxidized fatty acid esters and blends of such esters are provided, along with plasticized polymer compositions (especially phthalate- or substantially phthalate-free compositions) including the reduced color fatty acid ester or esters so made.

In either or both of the modified transesterification and interesterification processes of the present invention, a pretreatment of the borohydride may be used as exemplified below to improve the borohydride's color reducing or color formation inhibiting efficiency in the course of carrying out the transesterification or interesterification. In the interesterification example, where the borohydride is included without pretreatment, preferably a further additive such as a non-nucleophilic alcohol (for example, t-butanol) is instead included in the reaction mixture with the borohydride for the same purpose.

In commonly-assigned U.S. Pat. No. 7,126,018 to Poppe, it was discovered that polyol esters could be made that would not entail molecular distillations or further decoloration steps (e.g., carbon treatment, bleaching and the like) to provide a dihydroxy polyol ester product having a desirably light color. More particularly, it was determined that light color propylene glycol monoesters could be made that would be acceptable for use as non-volatile coalescing aids in latex paints, by reacting propylene glycol with a fatty acid ester, such as a vegetable oil fatty acid methyl ester or other fatty acid $C_1$-$C_5$ alkyl ester from a polyunsaturated vegetable oil, in the presence of a transesterification catalyst and borohydride. Other dihydroxy polyols mentioned included ethylene glycol, diethylene glycol and dipropylene glycol.

The present invention is based at least in part on the discovery that despite the labile nature of the epoxide functionality in the epoxidized natural fats or oils contemplated as starting materials, reduced color epoxidized fatty acid esters can also be made from an epoxidized natural fat or oil, through a transesterification process according to the first aspect or through an interesterification process according to the second aspect.

As well, the addition of the borohydride and starting from an epoxidized natural fat or oil does not appear to materially affect other commercially-relevant performance attributes of a plasticized polymer composition incorporating a reduced color epoxidized fatty acid ester of the present invention, as compared to an equivalent composition prepared using an epoxidized fatty acid ester made according to the known methods of Benecke et al. or the WO'877 application. Thus, as more particularly demonstrated in the examples below, an epoxidized methyl soyate (EMS) plasticizer made according to the present teachings demonstrates substantial equivalence in relevant performance attributes compared to an EMS plasticizer made by such a known method, but at the same time also provides improved Pt—Co color.

Given the indication in the WO'877 application that "epoxides made from esters of fatty acids such as the epoxidized methyl ester of soy oil are too volatile to serve as useful plasticizers of PVC," pg. 1, lines 30-31, this is a finding of considerable added importance for the specific reduced color epoxidized fatty acid ester, EMS. Rather than being dependent on the production economics or availability of biodiesel, which are in turn to some extent dependent on fuels demand, pricing and usage patterns, reduced color epoxidized methyl soyate esters may be made according to the present invention with an available supply of epoxidized soybean oil (the supply and demand for which is at least to some extent related to demand for the same plasticized PVC compositions in which ESO can be used as a secondary plasticizer and thermal stabilizer, and not to conditions in the fuel markets).

The capacity to make reduced color EMS and other epoxidized soybean oil ester derivatives from ESO is advantageous also, in the fact that the same ESO that would be used as the feed for making the reduced color EMS and low color epoxidized soybean oil derivatives may also be combined with the these products in the traditional role of ESO, as a secondary plasticizer and thermal stabilizer—so that the ESO may be both a feed and part of a reduced color, entirely renewable source-based, phthalate-free plasticizer system offering.

In general terms, and as mentioned above, the reduced color epoxidized fatty acid esters enabled by the present invention can be made by both transesterification and interesterification processes as desired. In a transesterification process according to a first aspect, an epoxidized natural fat or oil is combined with an alcohol, borohydride and a transesterification catalyst, and the epoxidized natural fat or oil and alcohol react to form an epoxidized fatty acid ester exhibiting a reduced Pt—Co color, as compared to the epoxidized fatty acid ester that would result from reacting the epoxidized natural fat or oil and the alcohol in the presence of the esterification catalyst and under the same conditions but without the use of borohydride. In one embodiment, borohydride is included in the reaction mixture with the epoxidized natural fat or oil and alcohol before introducing the catalyst. In an alternative embodiment, borohydride and catalyst are concurrently or substantially concurrently incorporated in the reaction mixture with the epoxidized natural fat or oil and alcohol. In still another embodiment, borohydride can be included both prior to and concurrent with the introduction of the catalyst. In any case, the borohydride is a lesser component of the reaction mixture as compared to the catalyst, as further elaborated below.

The degree of improvement in the Pt—Co color can be expected to depend upon the particular natural fat or oil used, among other considerations. Preferably, however, the process as just summarized will produce epoxidized fatty acid esters with a Pt—Co color (as determined in the manner illustrated in the Examples below) that is no more than 80 percent of the Pt—Co color of the material that would be produced without borohydride being used, more preferably being no more than 65 percent of the Pt—Co color of the material that would be produced absent the use of borohydride, and most preferably being no more than 50 percent of the Pt—Co color of that material.

Preferably, the degree of color improvement that is realized in the instant transesterification process context is such that the Pt—Co color of the reduced color epoxidized fatty acid ester is not greater than 150, more preferably is 90 or less and most preferably is 50 or less, so that the reduced color epoxidized fatty acid esters may be satisfactorily substituted for phthalate plasticizers with comparable Pt—Co color characteristics. In this regard, where inclusion of borohydride and a selection of the amounts of borohydride and other conditions of the tranesterification process do not provide a material meeting a desired Pt—Co color criterion, one or more other, known color removal techniques may be employed as well—for example, carbon treatment or bleaching.

The epoxidized natural fat or oil can be derived from animal or plant (including vegetable) sources. Preferably the epoxidized natural fat or oil is a vegetable or seed oil, for example, genetically modified oil, soybean oil, linseed oil, corn oil, sunflower oil, canola oil, rapeseed oil, coconut oil, palm kernel oil, palm oil, cottonseed oil, peanut oil, olive oil, tall oil, safflower oil and derivatives and mixtures thereof. Preferably, the oil is a polyunsaturated oil selected from the group above. Most preferably, the polyunsaturated oil is low in C18:3 or higher fatty acids. Although any polyunsaturated oil that has sufficiently low levels of C18:3 or higher fatty acids is suitable for the present method, preferably, the oil is safflower oil, sunflower oil or corn oil. Preferred oils contain less than 2 percent of C18:3 or higher polyunsaturated fatty acids. More preferably, the oils contain less than 1 percent of C18:3 or higher polyunsaturated fatty acids. Also preferred are polyunsaturated oils containing less than 2 percent linolenic acid. More preferably, the linolenic content is less than 1 percent.

The alcohol reactant for the transesterification may broadly be selected from any of the wide variety of aliphatic or cyclic monohydric, dihydric or polyhydric alcohols that will form an epoxidized fatty acid ester with the epoxidized natural fats or oils in the presence of a transesterification catalyst, though aromatic alcohols are less preferred. Monohydric aliphatic alcohols having from 1-20 carbon atoms are preferred, and while primary, secondary and tertiary alcohols may be considered, primary monohydric aliphatic alcohols are more preferred. Methyl, ethyl and benzyl primary monohydric aliphatic alcohols are particularly preferred, for providing reduced color epoxidized methyl, ethyl and benzyl soyate esters, for example.

The catalyst selected for use in the present method can be any catalyst that is suited for carrying out the transesterification reaction, and a number of such catalysts are known. Preferably, the catalyst used in the present process is an alkaline catalyst. More preferably, the catalyst is selected from the group consisting of sodium methoxide, sodium ethoxide, potassium methoxide, potassium ethoxide, potassium tert-butoxide or an N-heterocyclic carbene catalyst such as 1,3-Bis(2,6-diisopropylphenyl)imidazol-2-ylidene (CAS 244187-81-3), from Sigma-Aldrich Co. (though other N-carbene catalysts and preparation methods will be within the capabilities of those skilled in the art without undue experimentation). Most preferably, the catalyst used in the present process is sodium methoxide.

The borohydride material can be selected from the group consisting of sodium borohydride, potassium borohydride and lithium borohydride. By routine experimentation, a skilled artisan will quickly be able to determine the amount of borohydride that will produce a particular reduction in color, and whether additional known color removal techniques are desirably used. Preferably, the borohydride is present in an amount between 1.0 percent and 0.0001 percent by weight of the reactants and catalyst. More preferably, the amount of borohydride is between 0.1 percent to 0.001 percent. The catalyst in any event preferably comprises a greater part of the reaction mixture as compared to the borohydride, as greater amounts of borohydride can tend to inhibit the desired transesterification process without a corresponding degree of further improvement in the Pt—Co color of the product, or under circumstances where further improvements in the Pt—Co color are not really needed.

To help avoid a possible inhibitory effect of the borohydride on the transesterification of the epoxidized natural fat or oil with an alcohol, borohydride in one embodiment is included in the reaction mixture with the epoxidized natural fat or oil and alcohol before the catalyst is introduced and the transesterification process initiated. In an alternative embodiment, borohydride and catalyst are concurrently incorporated in the reaction mixture with the epoxidized natural fat or oil and alcohol—or sufficiently concurrently incorporated so that the borohydride does not materially inhibit the transesterification reaction in progress. In yet another embodiment, of course, an amount of borohydride can be introduced both prior to and concurrent with the introduction of the catalyst.

A pretreatment of the borohydride as exemplified below may also be employed, whereby the borohydride is combined with diglyme (diethylene glycol dimethyl ether) in solution for a time before being combined with the catalyst. In the interesterification context described more completely below, at least, a pretreatment of the borohydride in this manner is believed helpful for avoiding some inhibitory effect of the borohydride in relation to the interesterification catalyst and process, though as just indicated a pretreatment of the borohydride may be used in the instant transesterification context as well.

In terms of the process conditions used, the combined epoxidized natural fat or oil and alcohol are heated in the presence of the transesterification catalyst and borohydride to effect a transesterification of the epoxidized natural fat or oil. Preferably, the combined starting materials are heated to a temperature between 40° C. and 70° C. under a slight vacuum in an inert atmosphere, such as $N_2$, Ar or $CO_2$. More preferably, the temperature range is from 40° C. to 55° C. The reactants are preferably used neat and the reaction is carried out in the absence of moisture, with continuous agitation. It is preferred that the atmosphere is free of $O_2$ and is composed of an inert gas such as those listed above. The combined mixture is heated slowly to the above temperature range. During the process of transesterification, the temperature is maintained in the above range until sufficient conversion to product has occurred; preferably the reaction will be continued until substantially completed. The reaction mixture is then cooled and the catalyst is neutralized with acid, such as citric acid or phosphoric acid. The reduced color epoxidized fatty acid ester product can then be separated from the residual unreacted epoxidized natural fat or oil by conventional means.

The reduced color epoxidized esters of the present invention (made by either transesterification or interesterification) can be contemplated for use as primary or secondary plasticizers in a variety of polymers, including halogenated polymers, acid-functionalized polymers, anhydride-functionalized polymers, and nitrile rubbers. An exemplary halogenated polymer is a PVC polymer, where "PVC" or "polyvinyl chloride" as used herein is understood to cover the range of homo- and copolymers of vinyl chloride with typically up to 20% of comonomers such as vinyl acetate, propylene, ethylene, diethyl maleate, dimethyl fumarate and other ethylenically unsaturated comonomers. Examples of other halogenated polymers include polyvinyl halide polymers, chlorinated polyolefins and chlorinated rubbers. Suitable acid-functionalized polymers include acrylic acid-functionalized polymers, as well as acrylic and other polymers in need of plasticization to reduce glass transitions or improve toughness.

Where used as primary plasticizers, the reduced color epoxidized fatty acid esters can comprise preferably at least 20 percent by weight of a polymer composition, more preferably will comprise at least 30 percent by weight of a polymer composition, and most preferably will comprise at least 50 percent by weight of a polymer composition.

The plasticized polymer compositions of the present invention can be formulated, it is noted, in all other respects in a conventional manner, including various kinds of additives in addition to the inventive reduced color epoxidized esters. When the reduced color epoxidized esters are used in preferred embodiments as the primary plasticizers of a primary/secondary plasticizer system, for example, a renewably-based secondary plasticizer and thermal stabilizer such as epoxidized soybean oil can be added, or other secondary plasticizers (including petroleum-based plasticizers) or other additives for improving one or more properties of heat stability, lubricity or weathering resistance, as ultraviolet absorbers, fillers, anti-oxidants, anti-static agents, anti-fogging agents, pigments, dyestuffs, crosslinking aids and the like can be incorporated in the compositions. The inventive reduced color epoxidized esters may also be used in certain embodiments in combination with other primary plasticizers such as dioctylphthalate, other phthalates, citrates, benzoates, trimellitates, and other aliphatic diesters, though preferably the plasticized polymer compositions of the present invention will not include any added phthalates and will include substantially only renewably-based or biobased plasticizers.

Polymer compositions prepared using the reduced color epoxidized fatty acid esters of the present invention as a primary plasticizer, and preferably including ESO or some other biobased secondary plasticizer, will find commercial application in a variety of end uses wherein color (or the substantial absence of color) is important. Examples of suitable end uses are inks, plastisols, vinyl compounding, wire coating, medical devices, flooring, toys, and automotive parts and interiors.

In an interesterification process according to a second aspect of the present invention, an epoxidized natural fat or oil is combined with a second ester, borohydride and an interesterification catalyst, and the epoxidized natural fat or oil and second ester react to form an epoxidized fatty acid ester or ester blend exhibiting a reduced Pt—Co color, as compared to the epoxidized fatty acid ester or ester blend that would result from reacting the epoxidized natural fat or oil and the second ester in the presence of the interesterification catalyst and under the same conditions but without the use of borohydride. In one embodiment, borohydride is included in the reaction mixture with the epoxidized natural fat or oil and second ester before introducing the catalyst. In an alternative embodiment, borohydride and catalyst are concurrently incorporated (or substantially so) in the reaction mixture with the epoxidized natural fat or oil and second ester. In still another embodiment, borohydride can be included both prior to and concurrently with the introduction of the interesterification catalyst. In any case, the borohydride is a lesser component of the reaction mixture as compared to the catalyst, as further elaborated below.

The borohydride may be pretreated and introduced into the reaction mixture in a diglyme solution, for example, but if not pretreated accordingly will preferably be accompanied in the reaction mixture by a further additive such as a non-nucleophilic alcohol (e.g., t-butanol). Alternatively, the further additive may be used without a pretreatment step. In examples below, interesterifications were conducted which didn't appear to provide an appreciable improvement in Pt—Co color merely because of the use of borohydride. Where a pretreatment step was included, a degree of improvement was noted, but Pt—Co colors were still higher compared to the starting ESO material and compared to the phthalate plasticizers targeted for replacement. Where a further additive was included in the form of t-butanol, however, a Pt—Co color approximately equal to and better than that exhibited by the starting ESO material could be realized.

Preferably, as in the transesterification context, the epoxidized fatty acid esters or ester blends produced in the interesterification will exhibit a Pt—Co color that is no more than 80 percent of the Pt—Co color of the material that would be produced without borohydride being used, more preferably being no more than 65 percent and most preferably being no more than 50 percent of the Pt—Co color of that material.

Preferably, the degree of color improvement that is realized in the interesterification process context is such that the Pt—Co color of the reduced color epoxidized fatty acid ester or ester blend is not greater than 200, more preferably is 90 or less and most preferably is 50 or less, so that the reduced color epoxidized fatty acid esters may be satisfactorily substituted for phthalate plasticizers with comparable Pt—Co color characteristics. In this regard, where inclusion of pretreated borohydride and/or of further additives such as the non-nucleophilic alcohols, a selection of the amounts of borohydride and/or further additives and other parameters of the interesterification do not provide a material meeting a desired Pt—Co color criterion, one or more other, known color removal techniques may be employed as well—for example, carbon treatment or bleaching.

The epoxidized natural fat or oil can be as described previously, as can the borohydride. The second ester may broadly be selected from any of the wide variety of aliphatic or cyclic monoesters, diesters or polyesters that will undergo an interesterification with the epoxidized natural fat or oil and provide epoxidized fatty acid esters of interest for a given application, but in regard to making epoxidized fatty acid esters especially for use as primary plasticizers for PVC, the acetate esters of aliphatic and aromatic alcohols, including particularly the methyl, ethyl and benzyl acetates, are preferred.

The catalyst can be any catalyst that is suited for carrying out the interesterification reaction, and a number of such catalysts are known. Preferably, the catalyst used in the present process is an alkaline catalyst. More preferably, the catalyst is selected from the group consisting of sodium methoxide, sodium ethoxide, potassium methoxide, potassium ethoxide, potassium tert-butoxide or an N-heterocyclic carbene catalyst such as 1,3-Bis(2,6-diisopropylphenyl)imidazol-2-ylidene (CAS 244187-81-3), from Sigma-Aldrich Co. (though other N-carbene catalysts and preparation methods will be within the capabilities of those skilled in the art without undue experimentation). Most preferably, the catalyst used in the present process is sodium methoxide.

In terms of the process conditions used, the combined epoxidized natural fat or oil and second ester are heated in the presence of the catalyst and borohydride to effect an interesterification of the epoxidized natural fat or oil. Preferably, the combined starting materials are heated to a temperature between 40° C. and 70° C. under a slight vacuum in an inert atmosphere, such as $N_2$, Ar or $CO_2$. More preferably, the temperature range is from 40° C. to 55° C. The reactants are preferably used neat and the reaction is carried out in the absence of moisture, with continuous agitation. It is preferred that the atmosphere is free of $O_2$ and is composed of an inert gas such as those listed above. The combined mixture is heated slowly to the above temperature range. The temperature is maintained in the above range until sufficient conversion to product has occurred; preferably the reaction will be continued until substantially completed. The reaction mixture is then cooled and the catalyst is neutralized with acid, such as citric acid or phosphoric acid. The reduced color epoxidized fatty acid ester product can then be separated from the residual unreacted epoxidized natural fat or oil, for example, by liquid-liquid extraction as shown in the non-limiting examples below.

EXAMPLE 1

To a stirring solution of 500 milligrams of sodium methoxide in 100 grams of methanol was added 300 milligrams of sodium borohydride. This mixture was then added to a solution of 500 grams of epoxidized soybean oil in an additional 400 grams of methanol. The reaction mixture was stirred under argon and slowly heated to 45 degrees Celsius, and then maintained with stirring at 45 degrees Celsius for 3 hours.

Heating of the reaction mixture was discontinued, and the mixture allowed to cool to about 35 degrees Celsius, at which point a solution of 10 grams of citric acid in water was added to neutralize the mixture. After 10 minutes with stirring, the flask contents were transferred to a separatory funnel. About 100 mL of deionized water were added to generate distinct, separable organic and aqueous phases. After recovering the organic phase and washing 3 times with additional deioinized water (with iterative recoveries of the organic phase after each washing, of course), the organic layer was dried over anhydrous magnesium sulfate. The drying agent was removed by filtration, and the resulting product—a light colored viscous oil—was dried under vacuum overnight.

The dried EMS product was analyzed by 1H NMR, and the hydroxyl and acid values determined by the standard refined oils industry tests AOCS Tx 1a-66 and AOCS Te 2a-64, respectively. Iodine values were determined by AOCS method Cd 1-25, oxirane oxygen values were determined by AOCS method Cd 9-57, and the Pt—Co Hazen color of the product was determined according to ASTM D1209.

Results of this testing showed an average hydroxyl value of 0.4927, an acid value of 0.4446, an iodine value of 0.9048, an oxirane oxygen value of 6.5697 percent and a Pt—Co Hazen color of 57.

EXAMPLE 2

A reduced color epoxidized methyl soyate product was produced by compositing a number of EMS lots prepared as described herein. Specifically, the three EMS lots whose preparations are described in this Example 2 were composited with the EMS materials whose preparations are reported in Examples 7-9 below.

Of the three component lots dealt with by the present Example, two were identically-prepared. For these, 1500 grams of epoxidized soybean oil was first dried by heating the ESO to 85 degrees Celsius for one hour. The dried ESO was then added to a reactor along with 1500 grams of anhydrous methanol and stirred under a nitrogen blanket at 55 degrees Celsius. A mixture of sodium methoxide (4 g) and sodium borohydride (1 g) was added to the reactor. After stirring for an hour, NMR analysis showed the reaction as completed. The product mixture was then neutralized by a citric acid solution (25 g citric acid) in methanol, and excess methanol was removed under vacuum. A glycerol phase was formed, settled to the bottom of the reactor and removed. The remaining organic phase was washed three times with deionized water, and then dried with magnesium sulfate. Upon removal of the magnesium sulfate by filtration, the EMS product remaining was then dried under vacuum overnight. The third lot was prepared in the same way, except that the product mixture was neutralized by a solution of citric acid in water rather than of citric acid in methanol. The emulsion that formed in the third lot (after neutralization and following the removal of the excess methanol) was allowed to break, and the aqueous layer removed with processing of the remaining organic phase as in the first two lots. The Pt—Co Hazen color of the composited EMS sample thus prepared was determined to be 43 (by ASTM D1209).

COMPARATIVE EXAMPLE 1

For the "Control" EMS prepared according to known methods and included in a PVC composition for the comparison below in Examples 5 and 6 to PVC compositions including the reduced color EMS materials prepared in Examples 1 and 2, the transesterification method described in the '753 Benecke et al. patent (U.S. Pat. No. 6,797,753) beginning at column 3, line 30 was used. The resultant prior art EMS demonstrated a Pt—Co Hazen color of 103.

EXAMPLE 3

A solution of sodium borohydride (1 g, 0.026 M) in diglyme (10 mL) was added to epoxidized soybean oil (850 g) with stirring at 55° C. under $N_2$. The mixture was stirred vigorously for 1 hour, at which point anhydrous ethyl acetate (150 g, 1.7 M) was added. To the mixture was then added sodium methoxide in methanol (30%, 3 g NaOMe, 0.056 M). The reaction mixture was stirred vigorously for 3 hours.

The reaction was completed with full consumption of the ethyl acetate, as confirmed by $^1H$ NMR analysis. The product mixture was neutralized by addition of citric acid solution (20 g citric acid, 0.1 M). To the mixture was added petroleum ether (500 mL). The mixture was added to a separatory funnel and two phases were formed. The aqueous phase was removed and the organic phase was washed 3 times with deionized water. The organic phase was dried with magnesium sulfate and filtered. The petroleum ether was removed under reduced pressure yielding an epoxidized mixed ester interesterification product.

The Pt—Co color of the mixed ester product was then determined to be 139 according to ASTM D1209, compared to a Pt—Co color of the starting ESO material of 105.

EXAMPLE 4

A further interesterification was performed for this Example using a non-nucleophilic alcohol as a further additive. ESO (50 grams, 0.53 mols) was first dried under vacuum at 130° C. for 30 minutes. Ethyl acetate (108.43 mL, 97.80 grams) was washed with saturated potassium carbonate in water, with magnesium sulfate, and distilled from calcium hydride onto dry 4 Å molecular sieves. The dry ESO and ethyl acetate were then added to a 250 round bottom flask equipped with a stir bar and a condenser, under a nitrogen atmosphere. T-butanol (11.47 mL, 8.89 grams) was dried over magnesium sulfate and distilled from calcium hydride onto 4 Å molecular sieves, then added by syringe into the flask followed by powdered potassium t-butoxide (0.38 grams) and sodium borohydride (0.12 grams). The reaction mixture was heated at 45° C. for 16 h. The reaction was neutralized with a solution of citric acid in water and then washed three times with water. The organic layer was then dried over magnesium sulfate and the excess ethyl acetate was removed on a rotary evaporator.

The interesterified product demonstrated a Pt—Co color of 88, as compared to a Pt—Co color of the starting ESO feed of 104.

COMPARATIVE EXAMPLE 2

Example 4 was reproduced with the exception that sodium borohydride was not added to the reaction. The Pt—Co of the interesterified product was 180, more than double the Pt—Co color number for Example 4.

COMPARATIVE EXAMPLE 3

The same procedure was followed as in Example 4 and Comparative Example 2, except that no sodium borohydride or t-butanol were added and the reaction was held at reflux for the reaction period. The Pt—Co color of the interesterified product was high at 480, as compared to the starting ESO feed at 104.

EXAMPLES 5 AND 6

For Examples 5 and 6, plasticized PVC compositions were prepared from the prior art method EMS from Comparative Example 1 and from the inventive reduced color epoxidized methyl soyates prepared in Examples 1 and 2, respectively. The "Control" PVC composition corresponding to the prior art method EMS and the PVC compositions for Examples 5 and 6 each were comprised of 100 parts by weight of Geon™ 121 AR homopolymer PVC dispersion resin from PolyOne, Inc., Avon Lake, Ohio, with 70 parts by weight of the EMS plasticizer in question, and 2 parts by weight of Therm-Chek™ LOHF 120 Ba/Zn stabilizer (Ferro, Inc., Cleveland Ohio). Weighed powdered solids were introduced to a 1-gallon mixing bowl. These materials were combined with stirring at the lowest speed of a 3-Speed Hobart Paddle Mixer, slowly adding liquid components to solid components. The contents were mixed for about 30 minutes, and the mixture was subjected to vacuum (such as in a large dessicator) to reduce air entrapment.

Several tests were carried out on the PVC compositions, according to the following protocols:

Paste Viscosity—The paste viscosity of a plastisol specimen describes the flow behavior of plastisols under low shear. The suitability of a dispersion resin for a given application depends on the viscosity characteristics of the plastisol and indicates performance in pouring, casting, molding, and dipping processes. The Paste Viscosity Test (Brookfield Viscosity Test) was carried out substantially according to ASTM procedure D1824 using a Brookfield RVFD Viscometer. Measurements were made at room temperature at 2 revolutions per minute (RPM) and 20 RPM. Low initial paste viscosity is desired for ease of handling, with preferably as little increase as possible over time, so that the paste viscosity measurements were repeated on several occasions over a period of 28 days to determine the stability of the paste viscosity of the plastisol specimens.

Air Release—The Air Release Test is carried out to determine the relative speed of release of entrained air from a plastisol. Liquid plastisol is poured into at 4 ounce polypropylene cup or equivalent and the plastisol is stirred vigorously with a spatula for one minute. As the entrapped air rises to the surface, the rate at which the bubbles break is observed and recorded. A relative rating of "Excellent" to "Poor" is assigned by comparison with reference formulations. "Excellent" air release (5 minutes) is obtained with a reference formulation comprising 100 parts Geon™ 121AR resin, 67 parts diisononyl phthalate (DINP), 3 parts epoxidized soybean oil (ESO), and 2 parts Therm-Chek™ LOHF 120 stabilizer. "Poor" air release (more than 60 minutes) is obtained with a reference formulation comprising 100 parts Geon™ 121AR resin, 67 parts benzyl butyl phthalate (BBP), 3 parts ESO, and 2 parts Therm-Chek™ LOHF 120 stabilizer.

Hardness—The Shore A Hardness test is carried out substantially according to ASTM D2240 using a Shore Durometer Gage to determine the hardness values of plastisols. Hardness is a measure of the efficiency of the plasticizer. At equal levels of incorporation of two different plasticizers in otherwise identical plastisols, the plasticizer yielding the softer plastisol is a more efficient plasticizer.

Heat Stability—The Metrastat Heat Stability test is used to measure the thermal stability of a plastisol film at high temperatures. Fused sheets of plastisols are prepared and exposed to high temperatures for varying time periods along the length of the strips. An excellent plastisol does not discolor or char and maintains flexibility after the test. Fused sheets of plastisol are prepared by "drawing down" plastisol onto a heat-stable surface (release substrate) using a 20 mil (0.020") drawing bar; the release substrate must be capable of withstanding at least 200° C. (390° F.) for 5 minutes. The fused sheets ("draw downs") are fused for 3 minutes in an oven at 200° C. (390° F.). Fused sheets are allowed to cool at room temperature for a minimum of 15 minutes before removing from the release substrate. Sample strips measuring 25 cm (9.75 inch) by 2.5 cm (1 inch) are cut from the fused sheets. A Metrastat™ oven is preheated to 191° C. (375° F.) and sample strips are placed onto the travelling tray of the Metrastat™ oven. A one hour exposure cycle is started. As the tray travels the sample strips are exposed to the oven temperature over a time gradient of 0-60 minutes. When the cycle is complete, sample strips are allowed to cool for 1 hour and mounted onto display paper which shows the time the sample was exposed to high heat.

Gelation—The gel curve and gelation temperature test is carried out to determine the viscosity of plastisols under increasing temperature with a CarriMed™ CSL-2 500 rheometer. The gelation temperature indicates the solvating power of the plasticizer; lower gelation temperatures indicate greater solvating power, and are preferred for convenience in applications such as screen printing, dip coating, and preparation of soft rubber compounds because less heat is needed to maintain low viscosity of the plastisols. The viscosity is plotted as a function of temperature, and analysis of the plot indicates an approximate gelation temperature. A 4 centimeter flat, steel spindle is attached to the rotor of the rheometer and the calibration routine is carried out to calibrate the spacing between the rheometer Peltier plate and the spindle. An increase in temperature from 20° C. to 100° C. (68° F. to 212° F.) at a rate of 0.1° C. (0.18° F.) per second with a constant shear rate of 5 sec-1 is programmed into the rheometer software. A 2 gram sample of plastisol is loaded onto the Peltier plate and the program is initiated. At the conclusion of the temperature ramp, the results are plotted as output of viscosity versus temperature on a semi-Log chart to produce a gel curve. Then, lines are hand-drawn asymptotically to the two sections of the gel curve, extending them toward the X axis until they intersect. The gel temperature is then approximated by noting the temperature corresponding to the intersection of the hand-drawn lines.

Heat Loss—The Heat Loss test is applied to fused plastisols to determine the percent loss of mass during heat aging. Low heat loss is desirable, as volatilized plasticizer can contaminate nearby surfaces, such as windshield interiors on new cars. Fused sheets of plastisol are prepared substantially as in the Heat Stability Test. Square samples (5.0 cm by 5.0 cm (2 inch by 2 inch)) are punched or cut and weighed to +/−0.0001 g. The samples are incubated in an 82° C. (180° F.) oven for 7 and/or 14 days, and cooled for 30 minutes before re-weighing. The heat loss is expressed as a percentage of the original weight of the sample.

Plasticizer Volatility—The Plasticizer Volatility test is used to determine the relative plasticizer volatility that may affect plastisol processing. Lower plasticizer volatility is desired, especially for compounded (extruded) plastisols. A 1-gram sample of plasticizer is accurately weighed (+/−0.0001 g) and incubated in an oven for 3 minutes at 204° C. (400° F.). The weight loss is determined and the percentage of weight loss is reported as plasticizer volatility.

Exudation Test—Fused plastisol discs are made in aluminum weighing dishes using from 15+/−0.5 grams of liquid plastisol. Three discs per plastisol sample are prepared. The plastisols are fused for ten minutes in an oven preheated to 400° F. The discs are cooled quickly in water and removed from the aluminum dishes. To determine exudation, a stack of two fused plastisol discs is incubated in a 180° F. oven for at least 4 weeks. The discs are examined after 24 hours and weekly for at least four weeks and compared with an identical reference strip kept at room temperature. The visible presence of exudation is noted, and the amount exuded is determined by visual inspection. Exudation values are assigned as falling into one of the following ranges: trace-light-moderate-heavy.

Certain results of the various tests are reported below in Table 1. The Pt—Co Hazen color values determined for the prior art and inventive reduced color plasticizers in Comparative Example 1 and Examples 1 and 2 are reproduced in Table 1, to allow a comparison of other performance attributes in PVC plastisols incorporating the prior art and the two inventive reduced color examples (Examples 5 and 6) having slightly differing degrees of color reduction.

TABLE 1

|  | Comp. Ex. 1 | Ex. 1/ Ex. 5 | Ex. 2/ Ex. 6 |
| --- | --- | --- | --- |
| Color (Pt—Co) | 103 | 57 | 43 |
| Air Release | Good | Good | Good |
| Hardness (Shore A) | 70 | 70 | 70 |
| Heat Loss @ 180° F. (%), 7 Day | 10.0% | 10.1% | 15.2% |
| Heat Loss @ 180° F. (%), 14 Day | 14.1% | 13.8% | 18.7% |
| Plasticizer Volatility (% loss) (3 min @ 400° F.) | 13.1% | 14.0% | 9.2% |
| Brookfield RV Viscosity |  |  |  |
| Spindle | 3 | 3 | 3 |
| Initial @ 20 rpm, cps | 1,010 | 1,495 | 1,015 |
| Initial @ 2 rpm, cps | 1,250 | 2,700 | 1,200 |
| Spindle | 3 | 3 | 3 |
| 1 Day @ 20 rpm, cps | 2,375 | 2,325 | 2,275 |
| 1 Day @ 2 rpm, cps | 3,150 | 3,600 | 3,100 |
| Spindle | 4 | 4 | 4 |
| 3 Day @ 20 rpm, cps | 4,020 | 4,140 | 4,160 |
| 3 Day @ 2 rpm, cps | 6,300 | 6,250 | 6,200 |
| Spindle | 4 | 4 | 4 |

TABLE 1-continued

|  | Comp. Ex. 1 | Ex. 1/ Ex. 5 | Ex. 2/ Ex. 6 |
|---|---|---|---|
| 7 Day @ 20 rpm, cps | 8,080 | 8,800 | 7,870 |
| 7 Day @ 2 rpm, cps | 14,900 | 15,600 | 13,600 |
| Spindle | 5 | 5 | 5 |
| 14 Day @ 20 rpm, cps | 16,260 | 15,560 | 15,560 |
| 14 Day @ 2 rpm, cps | 34,400 | 31,000 | 31,000 |
| Spindle | 6 | 6 | 6 |
| 21 Day @ 20 rpm, cps | 25,900 | 25,850 | 25,450 |
| 21 Day @ 2 rpm, cps | 63,000 | 63,000 | 54,000 |
| Spindle | 6 | 6 | 6 |
| 28 Day @ 20 rpm, cps | 44,600 | 41,050 | 41,550 |
| 28 Day @ 2 rpm, cps | 115,500 | 95,000 | 104,500 |

EXAMPLE 7

In a 5 liter round bottom flask setup with a heating mantle and controller were placed 1500 grams of PlasChek 775™ epoxidized soybean oil (Ferro Corporation, Cleveland, Ohio) along with a molar excess (1800 grams) of anhydrous methanol. Additional methanol (200 grams), sodium borohydride (2 g) and 30% sodium methoxide in methanol solution (20 grams) were premixed and then added to the flask. Nitrogen was bubbled through the mixture with stirring as heating was begun to 40 degrees Celsius. The nitrogen flow was then stopped. After three hours under the nitrogen blanket at 40-45 degrees Celsius with periodic checks of the reaction's progress by NMR, the reaction was complete, and the product mixture was cooled slightly to about 35 degrees Celsius and then neutralized with 40 grams of 50% citric acid in water. A series of washes with deionized water in a separatory funnel removed salts from the product mixture. The product mixture was dried over anhydrous magnesium sulfate powder, filtered and stripped of residual volatiles using a rotary evaporator. The EMS made in this fashion showed a Pt—Co Hazen color of 41 when tested according to ASTM D1209.

EXAMPLE 8

Example 8 was carried out in essentially the same fashion as Example 7, using 4000 grams of ESO, 4300 grams of anhydrous methanol and a premix of 200 grams of methanol, 53 grams of 30% sodium methoxide in methanol and 5.3 grams of sodium borohydride combined in a larger 12 liter round bottom flask. On completion of the reaction, with washing and drying as in Example 7, the EMS showed a Pt—Co color of about 45,

EXAMPLE 9

Example 8 was reproduced in the same apparatus, using the same materials and procedures. The EMS end product had a Pt—Co color of 44 when tested.

As can be observed from Examples 5 and 6 especially, notwithstanding a substantial reduction in the Pt—Co color of the plasticizers used in the several PVC plastisol compositions, the reported properties in Table 1 of the PVC plastisols themselves as made from the prior art and inventive reduced color plasticizers are quite comparable. Results not shown in Table 1—for the Metrastat heat stability, gelation/gel temperature and exudation—were likewise found to be very comparable.

What is claimed is:

1. A process of making a reduced color epoxidized fatty acid ester from an epoxidized natural fat or oil, comprising the steps of combining an alcohol, an epoxidized natural fat or oil and borohydride with a transesterification catalyst, under conditions which are effective for reacting the alcohol and epoxidized natural fat or oil to form an epoxidized fatty acid ester exhibiting a reduced Pt—Co color, as compared to the epoxidized fatty acid ester that would result from reacting the alcohol and epoxidized natural fat or oil in the presence of the catalyst and under the same conditions but without the use of borohydride.

2. A process according to claim 1, wherein the borohydride has been pretreated by combination with diglyme before being brought into intimate contact with the catalyst.

3. A process according to claim 1, wherein the borohydride is present in the reaction mixture at between 0.0001 and 1.0 percent by weight of the total.

4. A process according to claim 3, wherein the borohydride is between 0.001 percent and 0.1 weight percent of the total.

5. A process according to claim 1, wherein the borohydride is included in the reaction mixture with the epoxidized natural fat or oil prior to introduction of the catalyst.

6. A process according to claim 1, wherein the borohydride is included in the reaction mixture concurrently or substantially concurrently with the catalyst.

7. A process according to claim 1, wherein the Pt—Co color of the reduced color epoxidized fatty acid ester is no more than 80 percent of the Pt—Co color of the ester material that would be produced under the same conditions and using the same catalyst but without using the borohydride.

8. A process according to claim 7, wherein the Pt—Co color of the product with borohydride is no more than 65 percent of the Pt—Co color that would be produced absent use of borohydride.

9. A process according to claim 7, wherein the Pt—Co color of the product with borohydride is no more than 50 percent of the Pt—Co color that would be produced absent use of borohydride.

10. A process according to claim 1, wherein the epoxidized fatty acid ester has a Pt—Co Hazen color of 90 or less as determined by ASTM D1209.

11. A process according to claim 10, wherein the epoxidized fatty acid ester has a Pt—Co Hazen color of 50 or less as determined by ASTM D1209.

12. A process of making a reduced color epoxidized fatty acid ester or mixture of esters from an epoxidized natural fat or oil, comprising the steps of combining an epoxidized natural fat or oil, a second ester and borohydride with an interesterification catalyst, under conditions which are effective for reacting the second ester and epoxidized natural fat or oil to form an epoxidized fatty acid ester or mixture of esters exhibiting a reduced Pt—Co color, as compared to the epoxidized fatty acid ester or mixture of esters that would result from reacting the second ester and epoxidized natural fat or oil in the presence of the catalyst and under the same conditions but without the use of borohydride.

13. A process according to claim 12, wherein the borohydride has been pretreated by combination with diglyme before being brought into intimate contact with the catalyst, or wherein the reaction mixture includes a non-nucleophilic alcohol, or wherein both conditions are met.

14. A process according to claim 12, wherein the borohydride is present in the reaction mixture at between 0.0001 and 1.0 percent by weight of the total.

15. A process according to claim 14, wherein the borohydride is between 0.001 percent and 0.1 weight percent of the total.

16. A process according to claim 12, wherein the borohydride is included in the reaction mixture with the epoxidized natural fat or oil prior to introduction of the catalyst.

17. A process according to claim 12, wherein the borohydride is included in the reaction mixture concurrently or substantially concurrently with the catalyst.

18. A process according to claim 12, wherein the Pt—Co color of the reduced color epoxidized fatty acid ester or mixture of esters is no more than 80 percent of the Pt—Co color of the ester material that would be produced under the same conditions and using the same catalyst but without using the borohydride.

19. A process according to claim 12, wherein the Pt—Co color of the product with borohydride is no more than 65 percent of the Pt—Co color that would be produced absent use of borohydride.

20. A process according to claim 12, wherein the Pt—Co color of the product with borohydride is no more than 50 percent of the Pt—Co color that would be produced absent use of borohydride.

21. A process according to claim 12, wherein the epoxidized fatty acid ester has a Pt—Co Hazen color of 90 or less as determined by ASTM D1209.

22. A process according to claim 21, wherein the epoxidized fatty acid ester has a Pt—Co Hazen color of 50 or less as determined by ASTM D1209.

* * * * *